United States Patent [19]

Wagman

[11] 4,210,161
[45] Jul. 1, 1980

[54] CREME RINSES WITH HAIR HOLDING PROPERTIES

[75] Inventor: Julius Wagman, Chicago, Ill.

[73] Assignee: Helene Curtis Industries, Inc., Chicago, Ill.

[21] Appl. No.: 921,555

[22] Filed: Jul. 3, 1978

[51] Int. Cl.² .......................... A45D 7/00; A61K 7/08
[52] U.S. Cl. ........................................ 132/7; 106/186; 106/197 R; 260/29.6 RW; 260/29.6 TA; 424/DIG. 2; 424/70; 424/71
[58] Field of Search ...................... 424/DIG. 2, 70, 71; 260/29.6 RW, 29.6 TA; 106/186, 197 R; 132/7

[56] References Cited

U.S. PATENT DOCUMENTS

| | | | |
|---|---|---|---|
| 3,630,654 | 12/1971 | Rosenthal et al. | 424/70 X |
| 3,655,865 | 4/1972 | Murphy | 424/70 X |
| 3,925,542 | 12/1975 | Viout et al. | 424/71 X |
| 3,959,461 | 5/1976 | Bailey et al. | 424/70 |
| 3,959,463 | 5/1976 | Neresian et al. | 424/70 |

Primary Examiner—Norman Morgenstern
Assistant Examiner—Vera C. Clarke
Attorney, Agent, or Firm—Dressler, Goldsmith, Shore, Sutker & Milnamow, Ltd.

[57] ABSTRACT

A creme rinse composition is provided for application to the hair for ease in combing and static control and to provide body and setting properties thereto comprising an aqueous composition containing from about 0.02 to about 2 weight percent of an anionic polymer and from about 0.1 to about 5 weight percent of a cationic surfactant capable of forming a water insoluble reaction product with said anionic polymer.

15 Claims, No Drawings

CREME RINSES WITH HAIR HOLDING PROPERTIES

BACKGROUND OF THE INVENTION

In the treatment and dressing of hair in a beauty salon, or at home, a creme rinse is conventionally applied to freshly shampooed and towel-dried hair to detangle the hair, reduce the static therein, and make it easier to comb. The creme rinse is left on the hair for a short time and is then rinsed from the hair.

The creme rinses available today are effective for the foregoing purposes, but leave the hair excessively soft and unable to hold a set.

Hair fixatives, such as polyvinylpyrrolidone have been added to creme rinses to provide body to the hair, but they have little effect because they are substantially rinsed out with the rinsing of the creme rinses.

SUMMARY OF THE INVENTION

In accordance with the present invention, a creme rinse compositon is provided for application to the hair comprising an aqueous composition containing from about 0.02 to about 2 weight percent of an anionic polymer and from about 0.1 to about 5 weight percent of a cationic surfactant capable of forming a water insoluble reaction product with said anionic polymer.

It has been found that the aforementioned insoluble reaction product is substantive to hair and remains on the hair to impart body and stiffness thereto, being detectable on the hair by a scanning electron microscope.

In a preferred aspect of this invention, the creme rinse composition contains a water-dispersible thickening agent to increase the viscosity of the composition and thereby keep the insoluble reaction product in suspension for prolonged periods. The preferred thickening agent is hydroxyethyl cellulose. Other suitable thickeners include gum arabic, gum karaya, ghatti gum, locust bean gum, guar gum, Irish moss, methyl cellulose, hydrolyzed starches and low molecular weight ethylene oxide polymers. The thickeners are suitable used in amounts from about 0.1 to about 5 percent by weight depending on the nature of the thickener and the viscosity desired. A preferred range is from about 0.2 to about 3 percent by weight.

Suitable cationic surfactants include quaternary ammonium chlorides and bromides having at least one long chain alkyl group or at least one aryl group. Specific surfactants which have been found suitable include oleyl dimethyl benzyl ammonium chloride, cetyl trimethyl ammonium chloride and methyl bis[2-hydroxyethyl] oleyl ammonium chloride. The cationic surfactant is generally used in amounts from about 0.1 to about 5 weight percent. A preferred range is from about 0.2 to about 3 weight percent by weight.

Suitable anionic polymers include vinyl polymers having a plurality of free carboxylic acid groups in the polymer chain, or alkali metal salts thereof. Specific anionic polymers which have been found to be useful include hydrolyzed copolymers of methyl vinyl ether and maleic anhydride, and the sodium salts of ethyl half esters of copolymers of methyl vinyl ether and maleic anhydride, the mol ratio of the methyl vinyl ether and maleic anhydride in these polymers ranging from 25:75 to 75:25. Hydrolyzed copolymers of ethylene and maleic anhydride in mol ratios ranging from 75:25 to 25:75 are also useful. Other useful anionic polymers include the sodium salts of terpolymers of octyl acrylamide, an acrylate ester and butylaminoethyl methacrylate; and acrylic acid polymers cross-linked with a polyfunctional agent such as a polyol or a polyamine. The anionic polymer is generally used in amounts from about 0.02 to about 2 weight percent, and preferably from about 0.05 to about 1 weight percent.

Sodium carboxymethyl cellulose may also be used as the anionic polymer in the compositions of this invention. Sodium carboxymethyl cellulose is known to be a thickening agent for aqueous systems. In combination with a cationic surfactant, however, it has little or no thickening effect unless it is used in substantial stoichiometric excess.

The relative proportions of anionic polymer and cationic surfactant are not critical. Satisfactory results are obtained with substantial stoichiometric excesses of either the anionic polymer or the cationic surfactant. It has also been found in compositions which have been centrifuged that the supernatant liquid is cationic even when the composition is made with a substantial stoichiometric excess of the anionic polymer.

The compositions may also contain coloring, perfumes and preservatives, if desired. Glutaraldehyde is a preferred preservative.

The compositions of this invention, when applied to freshly shampooed and towel-dried hair, and thereafter rinsed off, provide ease of detangling, ease of combing and static control and also body and set holding properties to the hair after drying. In addition, the compositions make the hair shaft surfaces resistant to the spread of sebaceous oils produced by the scalp and therefore tend to keep the hair cleaner for extended periods. The latter effect may be seen in photomicrographs which show a large contact angle between the hair and an oily material when a droplet of vegetable oil is applied to the hair.

EXAMPLE 1

A creme rinse formulation was prepared in accordance with the following formulation:

|   | Parts by Weight |
|---|---|
| Gantrez AN 119 (Note 1) | 0.29 |
| Ammonyx KP (Note 2) | 1.40 |
| Water | 98.31 |
|   | 100.00 |

Note 1 - totally hydrolyzed water soluble 50:50 molar copolymer of methyl vinyl ether and maleic anhydride with an average molecular weight of about 20,000.
Note 2 - oleyl dimethyl benzyl ammonium chloride - 50% active

EXAMPLE 2

A creme rinse formulation was prepared in accordance with the following formulation:

|   | Parts by Weight |
|---|---|
| Gantrez AN 119 | 0.18 |
| Ammonyx KP | 0.70 |
| Natrosol 250 HHR (Note 3) | 0.76 |
| Water | 98.36 |
|   | 100.00 |

Note 3 - hydroxyethyl cellulose

EXAMPLE 3

A creme rinse formulation was prepared in accordance with the following formulation:

| | Parts by Weight |
|---|---|
| Gantrez AN 119 | 0.15 |
| Barquat CT 429 (Note 4) | 1.21 |
| Natrosol 250 HHR | 0.75 |
| Water | 97.89 |
| | 100.00 |

Note 4 - cetyl triethyl ammonium chloride - 29% active

EXAMPLE 4

A creme rinse formulation was prepared in accordance with the following formulation:

| | Parts by Weight |
|---|---|
| Gantrez AN 119 | 0.15 |
| Ethoquad O/12 (Note 5) | 0.47 |
| Natrosol 250 HHR | 0.74 |
| Water | 98.64 |
| | 100.00 |

Note 5 - methyl bis[2-hydroxyethyl] oleyl ammonium chloride - 75% active

EXAMPLE 5

A creme rinse formulation was prepared in accordance with the following formulation:

| | Parts by Weight |
|---|---|
| Gantrez AN 119 | 0.200 |
| Ammonyx KP | 1.600 |
| Natrosol 250 HHR | 1.400 |
| Sodium Hydroxide | 0.034 |
| Glutaraldehyde | 0.050 |
| Water | 96.716 |
| | 100.00 |

EXAMPLE 6

A creme rinse formulation was prepared in accordance with the following formulation:

| | Parts by Weight |
|---|---|
| Gantrez AN 179 (Note 6) | 0.4 |
| Stearyl dimethyl benzyl ammonium chloride | 2.0 |
| Natrosol 250 HHR | 1.2 |
| Water | to 100.0 parts |
| NaOH | to adjust pH to 3.5-4 |

Note 6 - Totally hydrolyzed water soluble 50:50 molar copolymer of methyl vinyl ether and maleic anhydride with an average molecular weight of about 80,000

EXAMPLE 7

A creme rinse formulation was prepared in accordance with the following formulation:

| | Parts by Weight |
|---|---|
| Carboxymethyl cellulose | 0.20 |
| Ammonyx KP | 1.60 |
| Natrosol 250 HHR | 1.40 |
| Water | 96.80 |
| | 100.00 |

All of the above compositions provided ease of combability when applied to wet, towel-dried hair and provided hair holding properties when the hair was dried.

EXAMPLE 8

A creme rinse formulation was prepared in accordance with the following formulation:

| | Parts by Weight |
|---|---|
| Gantrez ES 225 (Note 7) | 0.4 |
| Ammonyx KP | 1.6 |
| Natrosol 250 HHR | 1.4 |
| Water | 96.6 |
| | 100.0 |

Note 7 - sodium salt of the ethyl half ester of 50:50 molar copolymer of methyl vinyl ether and maleic acid

EXAMPLE 9

A creme rinse formulation was prepared in accordance with the following formulation:

| | Parts by Weight |
|---|---|
| Carbomer 940 (Note 8) | 0.2 |
| Ammonyx KP | 1.6 |
| Natrosol 250 HHR | 1.4 |
| Glutaraldehyde | 0.05 |
| Water | 96.75 |
| | 100.00 |

Note 8 - polymer of acrylic acid cross-linked with a polyfunctional agent

EXAMPLE 10

A creme rinse formulation was prepared in accordance with the following formulation:

| | Parts by Weight |
|---|---|
| Amphomer (Note 9) | 0.2 |
| Ammonyx KP | 0.8 |
| Natrosol 250 HHR | 1.4 |
| Water | 97.6 |
| | 100.0 |

Note 9 - sodium salt of octyl acrylamide/acrylates/butyl aminoethyl methacrylate polymer All of the formulation of Examples 7 to 9 provided ease of combability when applied to wet, towel-dried hair and provided hair holding properties when the hair was dried.

EXAMPLES 11 to 13

Creme rinse formulations were prepared in accordance with the following formulations:

| | Parts by Weight | | |
|---|---|---|---|
| | Ex.11 | Ex.12 | Ex.13 |
| Natrosol 250 HHR | 1.4 | 1.4 | 1.4 |
| Gantrez AN 119 | 0.2 | 0.2 | 0.1 |
| Ammonyx KP | 1.6 | 0.8 | 1.6 |
| Water | 96.75 | 97.55 | 96.85 |
| Glutaraldehyde | 0.05 | 0.05 | 0.05 |
| | 100.00 | 100.00 | 100.00 |
| Mole Ratio = $\frac{\text{Equivalents AN 119}}{\text{Equivalents KP}}$ | 1.4 | 2.8 | 0.7 |

The formulations of Examples 11, 12 and 13 all provided ease of wet combing, ease of detangling, static control and stiffening of the hair. However, the formulation of Example 1 gave a greater stiffening effect than the formulation of Examples 12 or 13.

The formulations of Examples 11, 12 and 13 were made without thickener so that the solids therein could be readily separated by centrifugation. The formulations of Examples 11 and 12 were centrifuged for one hour to separate solids from supernatant liquids of milky appearance. The supernatant liquids were found to be cationic.

EXAMPLE 14

A creme rinse formulation was prepared in accordance with the following formulation:

|  | Parts by Weight |
| --- | --- |
| Methocel E4M (Note 10) | 1.4 |
| EMA-31 (Note 11) | 0.4 |
| Ammonyx KP | 3.2 |
| Water | 95.0 |
|  | 100.0 |

Note 10 - methyl cellulose having a viscosity of 4000 cp at 2% concentration in $H_2O$ at 20° C.
Note 11 - totally hydrolyzed water soluble 50:50 molar copolymer of ethylene oxide and maleic anhydride with an average molecular weight of about 100,000.

The composition provided ease of combability when applied to wet, towel-dried hair and provided hair holding properties when the hair was dried.

The invention has been described with respect to preferred embodiments. However, modifications within the gist of this invention will be apparent to those skilled in the art.

What is claimed is:

1. A creme rinse composition for application to the hair comprising an aqueous composition containing from about 0.02 to about 2 weight percent of an anionic polymer and from about 0.1 to about 5 weight percent of a cationic surfactant capable of forming and having formed a water insoluble reaction product with said anionic polymer, said reaction product being suspended in a liquid in said composition, which liquid consists essentially of water.

2. The creme rinse composition of claim 1 wherein said cationic surfactant is oleyl dimethyl benzyl ammonium chloride.

3. The creme rinse composition of claim 1 wherein said cationic surfactant is cetyl trimethyl ammonium chloride.

4. The creme rinse composition of claim 1 wherein said cationic surfactant is methyl bis[2-hydroxy] oleyl ammonium chloride.

5. The creme rinse composition of claim 1 wherein said composition contains from about 0.1 to about 5 weight percent of a thickening agent.

6. A creme rinse composition for application to the hair comprising an aqueous composition containing from about 0.02 to about 2 weight percent of an anionic polymer and from about 0.1 to about 5 weight percent of a cationic surfactant capable of forming and having formed a water insoluble reaction product with said anionic polymer, said reaction product being suspended in said composition, said anionic polymer being a hydrolyzed copolymer of methyl vinyl ether and maleic anhydride in a mol ratio from 25:75 to 75:25.

7. The creme rinse composition of claim 6 wherein said cationic surfactant is stearyl dimethyl benzyl ammonium chloride.

8. The creme rinse composition of claim 7 wherein said hydrolyzed copolymer is an equimolar copolymer having an average molecular weight of about 80,000.

9. The creme rinse composition of claim 2 wherein said cationic surfactant is oleyl dimethyl benzyl ammonium chloride.

10. The creme rinse composition of claim 9 wherein said hydrolyzed copolymer is an equimolar copolymer having an average molecular weight of about 20,000.

11. A creme rinse composition for application to the hair comprising an aqueous composition containing from about 0.02 to about 2 weight percent of an anionic polymer and from about 0.1 to about 5 weight percent of a cationic surfactant capable of forming and having formed a water insoluble reaction product with said anionic polymer, said reaction product being suspended in said composition, said anionic polymer being a sodium salt of an ethyl half ester of a copolymer of methyl vinyl ether and maleic anhydride in a mol ratio from 25:75 to 75:25.

12. A creme rinse composition for application to the hair comprising an aqueous composition containing from about 0.02 to about 2 weight percent of an anionic polymer and from about 0.1 to about 5 weight percent of a cationic surfactant capable of forming and having formed a water insoluble reaction product with said anionic polymer, said reaction product being suspended in said composition, said anionic polymer being an acrylic acid polymer cross linked with a polyfunctional agent of the group consisting of polyols and polyamines.

13. A creme rinse composition for application to the hair comprising an aqueous composition containing from about 0.02 to about 2 weight percent of an anionic polymer and from 0.1 to about 5 weight percent of a cationic surfactant capable of forming and having formed a water insoluble reaction product with said anionic polymer, said reaction product being suspended in said composition, said composition containing from about 0.1 to about 5 weight percent of a thickening agent which is hydroxyethyl cellulose.

14. A creme rinse composition for application to the hair comprising an aqueous composition containing from about 0.02 to about 2 weight percent of an anionic polymer and from about 0.1 to about 5 weight percent of a cationic surfactant capable of forming and having formed a water insoluble reaction product with said anionic polymer, said reaction product being suspended in said composition, said anionic polymer being sodium carboxymethyl cellulose.

15. In the method of dressing hair wherein towel-dried hair is wetted with a creme rinse composition and thereafter rinsed, combed, set and dried, the improvement wherein said creme rinse composition is an aqueous composition containing from about 0.02 to about 2 weight percent of an anionic polymer and from about 0.1 to about 5 weight percent of a cationic surfactant capable of forming and having formed a water insoluble reaction product with said anionic polymer, said reaction product being suspended in said composition.

* * * * *